(12) United States Patent
Murata (10) Patent No.: US 7,960,185 B2
(45) Date of Patent: Jun. 14, 2011

(54) PROTEIN-IMMOBILIZED CARRIER

(75) Inventor: Yusuke Murata, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/279,334

(22) PCT Filed: Nov. 29, 2007

(86) PCT No.: PCT/JP2007/073534
§ 371 (c)(1),
(2), (4) Date: Aug. 13, 2008

(87) PCT Pub. No.: WO2008/069258
PCT Pub. Date: Jun. 12, 2008

(65) Prior Publication Data
US 2009/0234107 A1   Sep. 17, 2009

(30) Foreign Application Priority Data

Dec. 4, 2006  (JP) ................................. 2006-327461

(51) Int. Cl.
*B01D 21/00* (2006.01)
(52) U.S. Cl. ..... 436/527; 436/518; 436/524; 435/283.1; 435/287.1; 435/288.7
(58) Field of Classification Search ............. 436/518, 436/524, 527; 435/283.1, 287.1, 288.7
See application file for complete search history.

(56) References Cited

U.S. PATENT DOCUMENTS

| | | | | |
|---|---|---|---|---|
| 5,364,797 A | * | 11/1994 | Olson et al. | 436/501 |
| 5,980,849 A | * | 11/1999 | Ogata et al. | 423/332 |
| 6,846,546 B2 | | 1/2005 | Kuroda et al. | |
| 7,563,451 B2 | * | 7/2009 | Lin et al. | 424/400 |
| 2003/0109062 A1 | * | 6/2003 | Inomata et al. | 436/518 |
| 2005/0025690 A1 | * | 2/2005 | Fukuda et al. | 423/335 |
| 2006/0120955 A1 | * | 6/2006 | Miyata | 423/702 |
| 2007/0148044 A1 | | 6/2007 | Murata | |
| 2007/0298480 A1 | | 12/2007 | Murata | |

FOREIGN PATENT DOCUMENTS

| | | |
|---|---|---|
| JP | 7-122622 B | 12/1995 |
| JP | 2004-83501 A | 3/2004 |

OTHER PUBLICATIONS

PCT International Search Report and Written Opinion of the International Searching Authority, Mailing Date Mar. 20, 2008.
Zhang, et al., "Unusual Mesoporous SBA-15 with Parallel Channels Running along the Short Axis", J. Am. Chem. Soc., vol. 126, 2004, pp. 7440-7441.
Hu, et al., "Adsorption and Activity of a Domoic Acid Binding Antibody Fragment on Mesoporous Silicates", J. Phys. Chem. B, vol. 110, 2006, pp. 18703-18709.
Ding, et al., "Siilca nanotubes for lysozyme immobilization", Journal of Colloid and Interface Science, vol. 290, 2005, pp. 102-106.
Mercuri, et al., "Ordered Mesoporous Silica SBA-15: A New Effective Adjuvant to Induce Antibody Response", Small, 2006, vol. 2, No. 2, pp. 254-256.
Katiyar, et al., "Visualization of Size-Selective Protein Separations on Spherical Mesoporous Silicates", Small, vol. 2, No. 5, pp. 644-648, 2006.
Ye, et al., "Polyvalent Carbocyanine Molecular Beacons for Molecular Recognitions", J. Am. Chem. Soc. 2004, vol. 126, pp. 7740-7741.

* cited by examiner

Primary Examiner — Melanie J Yu
(74) Attorney, Agent, or Firm — Fitzpatrick, Cella, Harper & Scinto (57) ABSTRACT

The present invention provides a protein-immobilized carrier which can realize highly efficient use of an immobilized antibody and prevent non-specific binding. A protein-immobilized carrier including a porous body having mesopores characterized in that the carrier has mesopores having an organic substance adsorbed therein other than an antibody, an antigen or a fragment thereof having a particle size smaller than the pore size of the mesopores and having an antibody, an antigen or a fragment thereof physically adsorbed and immobilized from the pore entrance to a depth of not more than the pore size in the depth direction of the mesopores.

12 Claims, 7 Drawing Sheets

PROTEIN-IMMOBILIZED CARRIER

TECHNICAL FIELD

The present invention relates to a protein-immobilized carrier for detecting an antigen-antibody reaction, and particularly to a protein-immobilized carrier for detecting an antigen-antibody reaction including a porous body having an antibody carried on a solid phase thereof and the reaction is efficiently performed.

BACKGROUND ART

Generally, the content or the like of minor substances contained in a biological sample such as serum and urine, for example, a protein, is determined by immunoassay, which utilizes an antigen and/or an antibody. The immunoassay utilizes the fact that a binding reaction between an antigen and an antibody corresponding thereto proceeds very specifically and occurs even at low concentrations. Generally, two methods, a sandwich method and a competition method, are known, but an immobilized (solid-phased) antibody or antigen and a labelled antibody or antigen are used in many cases.

Meanwhile, immobilization of these antibodies, that is, immobilization of an antibody to a material or a member having a certain shape is performed routinely in immunoassay, an immune sensor and the like. A latex or polystyrene tube or the like is commonly used as a carrier for immobilizing an antibody. In addition to these, for example, a fibroin film disclosed in Japanese Patent Publication No. H07-122622 and a mesoporous silica porous body disclosed in Japanese Patent Application Laid-Open No. 2004-083501 are exemplified.

DISCLOSURE OF THE INVENTION

Intrinsically, since the reaction rate between an antigen and an antibody is extremely fast and the binding constant of a complex of an antigen and an antibody is as high as $10^{12}$ L/mol, measurement shall be performed rapidly and quantitatively even if the concentration of a target substance of the measurement, an antigen or the like is low.

In actual immunoassay, however, the lower limit of the measurement at which an antigen can be detected is determined by various factors. Representative factors include (1) a factor of non-specificity that a labelled antibody may directly bind to immunoassay apparatus, for example, carriers for immobilization; (2) a factor of reproducibility in a plurality of measurements; and (3) a factor of poor immunoreactivity that the detection amount by the reaction is small.

As for (1), there have been conventionally investigated methods in which an antibody is labeled so that non-specific binding may hardly occur; a binding partner in the reaction is modified so that binding may hardly occur; and further a reagent which inhibits non-specific binding is added and the like, and these methods have produced good results. Besides, when the mesoporous silica mentioned above is used as a carrier for immobilization, an antibody is adsorbed within pores to stabilize the antibody while restricting the reaction field of the antigen-antibody reaction to a nano-size space within the pores. The space within the mesopores, however, strongly trap adsorbed species by physical interaction such as van der Waals interaction as compared with normal solid surface. Therefore, it has been difficult to discriminate specific binding between an antigen and an antibody from non-specifically bound adsorbed species merely trapped within mesopores, even if a step such as washing is used.

On the other hand, as for (3) in particular, there have been merely investigated a method in which an antibody having a larger affinity constant to an antigen is used; and a method in which a monoclonal antibody is used in place of a polyclonal antibody. In late years, monoclonal antibodies having a larger affinity constant have been reported, and the factor (3) regarding the reactivity has been improved. However, acquisition of a monoclonal antibody having a large affinity constant has difficulties such as preparation of an extremely large number of hybridomas and screening a hybridoma which produces the above monoclonal antibody from among them. In addition, the specific monoclonal antibody has a binding ability only for a specific antigen, and therefore, in order to improve the factor (3) in immunoassay for various antigens, monoclonal antibodies having higher affinity have to be prepared for respective measurement.

Furthermore, when antibodies are immobilized on the surface of a carrier for immobilization, a simple adsorption method is frequently adopted, but the orientation at the binding sites is random in many cases in the immobilization of an antibody onto a solid phase carrier. Generally, it is said that the antibodies immobilized on the surface of a solid phase keeping a variable region in an available spacial configuration is around 20%, and it is pointed out as one of the factors for decreasing immunoreactivity.

The present invention has been made in view of the above problems, and solutions for improving the above factors (1) and (3) without preparing monoclonal antibodies having high affinity for every measurement in immunoassay for various antigens have been investigated intensively.

The present invention provides a protein-immobilized carrier which can realize highly efficient use of an immobilized antibody and prevent non-specific binding by using the surface of mesopores of a porous body such as mesoporous silica as a carrier for immobilization of the antibody.

The present invention is directed to a protein-immobilized carrier comprising a porous body with mesopores, the mesopores adsorbing inside at least one selected from the group consisting of an antibody, an antigen and an organic substance other than a fragment of the antibody or the antigen which has a particle diameter smaller than a size of the mesopores, and, at least one selected from the group consisting of an antibody, an antigen and a fragment of the antibody or the antigen being physically adsorbed and immobilized on a region of the mesopore from an entrance of the pore to the same depth as the size of the mesopores.

In the protein-immobilized carrier, a part of the mesopores can adsorb only the organic substance other than the antigen, the antibody and the fragment of the antibody or the antigen, and, the antibody, the antigen and the fragment are not immobilized.

The size the pore can be in the range of 7 nm to 30 nm.

The mesopores can have a length of 5 times and 30 times of the pore size.

The mesopores can be disposed in a honeycomb shape.

The mesopores can have a pore size distribution determined by nitrogen gas adsorption measurement having a single maximum and not less than 60% of all the mesopores fall within the pore size distribution range of not more than 10 nm.

In the protein-immobilized carrier, at least one diffraction peak in X-ray diffraction analysis can exist in an angle region corresponding to a structural period of not less than 1 nm.

In the protein-immobilized carrier, a material constituting a pore wall of the porous body can comprise silicon as an ingredient. The material constituting a pore wall can be silica.

The organic substance can be a protein.

According to the present invention, an antibody, an antigen or a fragment thereof is immobilized by physical adsorption within a mesopore from a pore entrance to a depth of not more than the diameter of the pore in the depth direction of the mesopore.

Consequently, large deformation of an antibody or the like at a molecule level is physically controlled within the pore, and the active steric conformation of the antibody is maintained stably. In addition, mesopores which do not contribute to an antigen-antibody reaction are buried by having adsorbed an organic substance such as a protein whose size is smaller than the pore size of the mesopores and thereby non-specific absorption can be significantly decreased.

Besides, an antibody itself can move flexibly to some extent even if variable region recognizing the target substance such as an antigen is immobilized within mesopores in a condition in which the variable regions are in random directions. Accordingly, in the case of an antigen-antibody reaction with a large binding constant, an antibody can be repositioned to a steric conformation so that the antibody can recognize the antigen while enabling specific binding. Therefore, an antibody on the solid phase which has not been able to contribute to specific binding can be used for the antigen-antibody reaction and the reactivity in immunoreaction between the antigen and the antibody can be improved.

As a result, the amount of detection signal for the measurement target at a low concentration increases particularly in immunoassay, and the lower limit of the measurement target can therefore be decreased to a lower concentration and improvement in sensitivity of the measurement system can be achieved. In addition, when a measurement target sample contains a great deal of proteins and the like as in the case of blood, the antigen-antibody reaction may be affected by the constituents thereof, which may vary depending on the sample and the condition of the patient. The present invention can reduce the influence due to such varying constituents.

Since the protein-immobilized carrier of the present invention can realize highly efficient use of an immobilized antibody and prevent non-specific binding by using the surface of mesopores of a porous body such as mesoporous silica as a carrier for immobilization of the antibodies, it can be used as a substrate for an antigen-antibody reaction.

Other features and advantages of the present invention will be apparent from the following description taken in conjunction with the accompanying drawings, in which like reference characters designate the same or similar parts throughout the figures thereof.

BEST MODES FOR CARRYING OUT THE INVENTION

Preferred embodiments of the present invention will now be described in detail in accordance with the accompanying drawings.

The protein-immobilized carrier according to the present invention is a protein-immobilized carrier including a porous body having mesopores and the carrier has an organic substance other than an antibody, an antigen or a fragment thereof in the mesopores. Furthermore, it is characterized by having mesopores having an antibody, an antigen or a fragment thereof physically adsorbed and immobilized from a pore entrance to a depth of not more than the pore size in the depth direction of the mesopores.

At first, a porous body having mesopores to be used in the present invention is described.

Figure 1A:
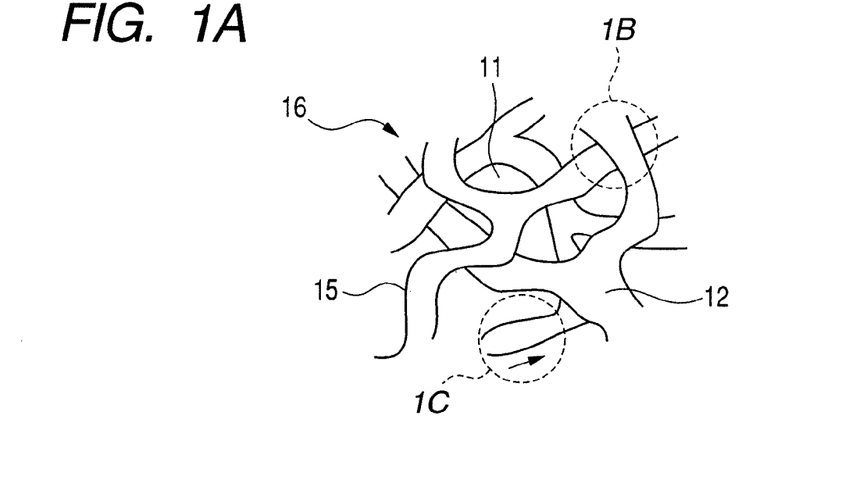
FIGS. 1A, 1B and 1C are schematic views illustrating an embodiment of a porous body of the present invention having mesopores constituted by dendritic mesoporous silica.
Figure 1B:
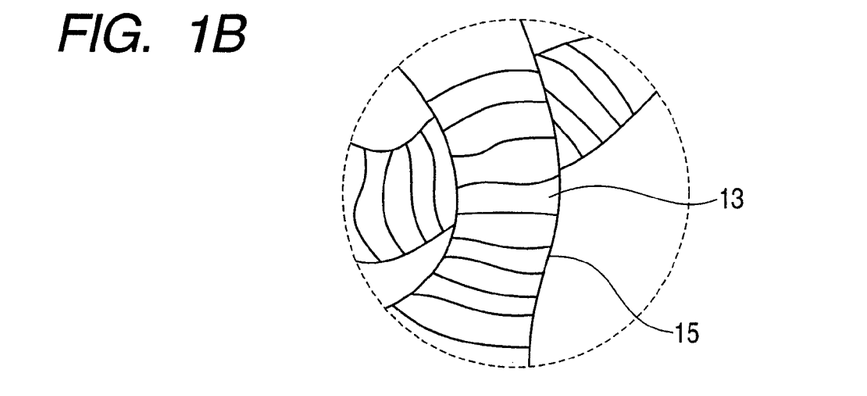
Figure 1C:
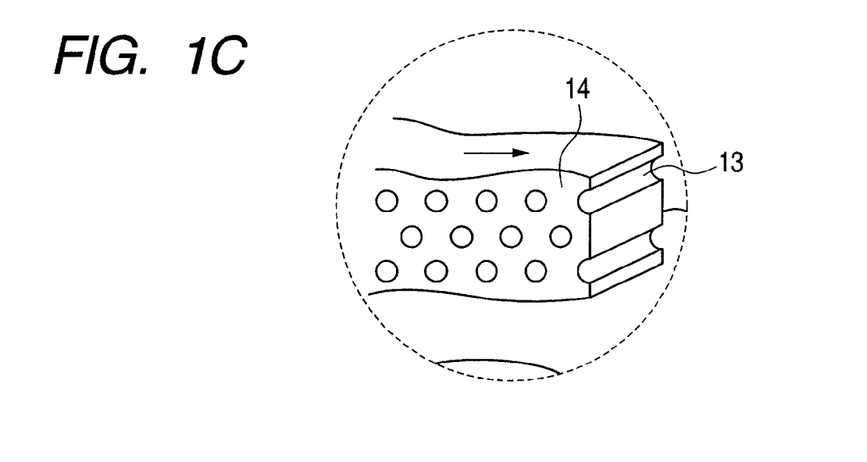

FIGS. 1A, 1B and 1C are schematic views illustrating an embodiment of a porous body of the present invention having mesopores constituted by dendritic mesoporous silica. In FIGS. 1A, 1B and 1C, as for porous body 16, rods 15 including silica having mesopores 13 branch to form a dendritic structure 12 and are three dimensionally disposed in the shape of a net, and macro pores 11 are formed in the spaces among the rods 15 of the dendritic structure 12. Tube-shaped mesopores 13 are disposed in parallel with the minor axis direction of the rod 15, and mesopores 13 are stacked in layers in the major axis direction of the rod 15. 14 designates the pore wall.

In the porous body 16, the dendritic structure 12 is entangled with each other three-dimensionally and forms a network-shaped structural body. Since the dendritic structure has no regular orientation, it does not take a closely packed packing structure. This is why the macropores 11 are formed in the spaces of the dendritic structure. If the porous body has such a shape, it has a number of mesopores 13 in which antibodies are immobilized and enables rapid diffusion when an antigen-antibody reaction occurs and such a structure is therefore preferable. The porous body can also be in other shapes such as a sphere or a membrane, however.

In the present invention, a mesopore is in accordance with the definition of IUPAC and refers to a pore having a pore size in the range from not less than 2 nm to not more than 50 nm. Preferably, the pore size of the mesopore is not less than 7 nm and not more than 30 nm. This is because unless the mesopore has a pore size equal to or more than the maximum diameter of an antibody and an antibody fragment, when an antibody adsorbed at random causes antigen-antibody reaction, a free degree of 360° cannot be secured and relocation of the antibody will be limited. It is also preferable that the length of the mesopores is not less than 5 times and not more than 30 times of the pore size. Since the immobilization is performed in the vicinity of the entrance of the mesopores, spaces other than the vicinity of the surface of the pore become useless even when the length of one pore is large. In addition, when mesopores oriented vertically on the substrate are used and the pore length is too small, it is considered that the effect of the present invention cannot be obtained due to influence of the substrate. As long as the pore has a structure mentioned above, the pore may have a structure with one end closed.

The mesopores of mesoporous particles can be formed by a surfactant molecular assembly (micelle). In a certain condition, since the number of molecules associated to form a micelle is constant pores with the same shape are formed. As the shape of the micelle, various shapes such as a sphere, a tube and a layer are known, but a micelle forming mesoporous material of the present invention basically has a tube shape. The tubes may be connected or separated. In the mesoporous material to be used in the present invention, any material forming a pore wall of the porous material can be adopted as long as it has a pore structure as mentioned above. Examples thereof include titanium oxide, tin oxide and silicon oxide. Among these, materials containing silicon as an ingredient are preferable, and silica can be used particularly preferably. The material may be an organic silica hybrid material composed of an organic group containing one or more carbon atoms, two or more silicon atoms bound to the above organic group at two or more sites and one or more oxygen atoms bound to the above silicon atom.

The method for forming the mesoporous material having a small aspect ratio between the pore size and the pore length which uses a surfactant micelle as a template is disclosed in the following documents. It is described in Journal of the American Chemical Society, Vol. 126, page 7740. However, the mesoporous material used in the present invention is not limited to these, as long as the characteristics of above mesoporous materials are satisfied.

Hereinbelow, a synthesis method of a minor axis oriented mesoporous silica using a sol-gel method is described.

The reaction solution is a solution containing a surfactant, an organic molecule and a material which can be a raw material of the object material such as a metal alkoxide. An acid or the like which serves as a hydrolysis reaction catalyst may be added in an appropriate amount depending on the material forming the wall of the pore.

Halides, chalcogen compounds, metal alkoxides and the like can be used as a raw material in accordance with the object material. For example, tetraethoxysilane and tetramethoxysilane which are metal alkoxides are preferably used when the wall of the pore is made of silica. Naturally, silica sources other than alkoxides can be adopted in the present invention.

Nonionic surfactants such as block copolymers containing polyoxyethylene as a hydrophilic group can be used as a surfactant. However, usable surfactants are not limited to these and not particularly limited, as long as the intended structure can be obtained.

A pore structure having a small aspect ratio can be controlled by the organic molecules to add and the addition amount thereof. For example, a rod-shaped mesoporous silica with a pore structure having a small aspect ratio can be synthesized by adding n-decane.

Common acids such as hydrochloric acid and nitric acid can be used as the acid.

The object mesoporous materials can be synthesized by reacting a reaction solution as mentioned above under a hydrothermal condition. The synthesis temperature is selected from the temperature range from not less than 80° C. to not more than 150° C. The reaction time is from several hours to several days, and the reaction temperature and the reaction time are optimized appropriately.

The mesoporous material synthesized in this way is washed with distilled water and then naturally dried in the air and thus an inorganic-organic composite powder material which contains surfactant micelles as templates within the pores is obtained. A mesoporous material usable in the present invention can be prepared by removing the surfactant micelle templates from the thus prepared inorganic-organic composite powder material. The method of removing the surfactant includes various methods, and any method may be used as long as it can remove the surfactant without destroying the pore structure.

The method most commonly used is burning in an oxygen-containing atmosphere. For example, the surfactant can be completely removed without substantial damage on the mesopore structure by burning the synthesized material in the air at 500° C. for ten hours. It is preferable that the burning temperature and time are optimized in accordance with materials constituting the pore wall and the surfactant used.

Information on the pore size of the mesoporous powder sample synthesized by such a method can be obtained by performing nitrogen gas adsorption-desorption measurement. It is characteristic of the pore size of mesoporous materials of the present invention that it is substantially a uniform diameter.

The distribution of the mesopores can be determined by conventional methods such as Berret-Joyner-Halenda (BJH) method. The pores with a uniform diameter as used herein have a single maximum value in the pore size distribution determined by evaluation by Berret-Joyner-Halenda (BJH) method based on the results of nitrogen gas adsorption measurement. Furthermore, it shows that mesopores of not less than 60% of all the mesopores are included in the pore size distribution range of not more than 10 nm. The pore size can be changed by appropriately selecting the surfactants described later.

Information on the structural period of the pores can be obtained by X-ray diffraction (XRD) measurement. The mesoporous materials in the present invention are characterized by having at least one diffraction peak in XRD measurement in an angle region corresponding to a structural period of not less than 1 nm.

Next, the protein-immobilized carrier of the present invention is described.

Figure 2:
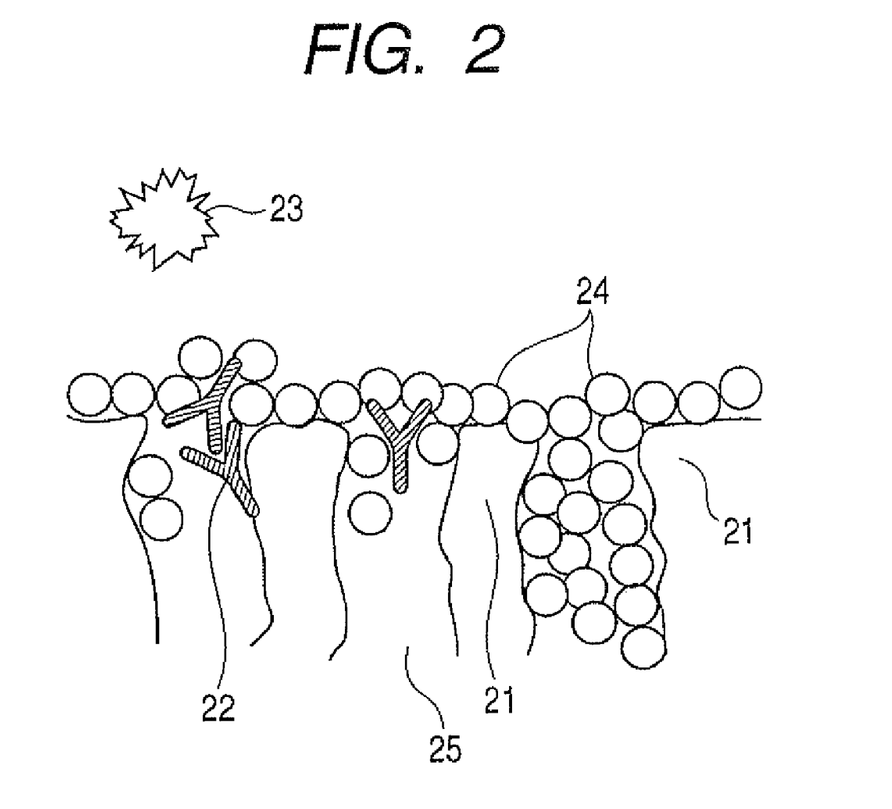
FIG. 2 is a schematic view illustrating a part of the protein-immobilized carrier which have antibodies, antigens or the fragments thereof immobilized within mesopores.

FIG. 2 is a schematic view illustrating a part of the protein-immobilized carrier which immobilized an antibody, an antigen or a fragment thereof within the mesopores. FIG. 2 includes pore walls 21 of a mesoporous material, an antibody, an antigen or a fragment thereof 22. The referential numeral 23 refers to an antigen having specific binding ability or a fragment having reaction specificity with the antibody. Also shown are a blocking agent 24 including a protein smaller than the pore size for preventing non-specific absorption and mesopores 25.

When an antibody is immobilized within mesopores, it is preferable to have the antibody physically adsorbed by electrostatic binding onto the inner surface of the pores. However, a biological substance can be held within mesopores not only by electrostatic binding but also by a van der Waals force, a hydrogen bond, or a non-covalent bond such as an ionic bond.

Substances to be immobilized may be an antigen, an antibody or a fragment containing an active site such as a Fab antibody. They may be extracted from animals, plants or microbes and may be cleaved as desired, or genetically or chemically synthesized.

In order to have antibodies physically adsorbed on the region from the entrance of the mesopores of the porous body to the depth of a pore diameter, a method of filling the pores with similar antibodies is used. In order to effectively introduce an antibody into the porous body, preferred is a method of adjusting a salt level and/or pH of a buffer solution to make an aqueous solution containing antibody to be in an electrically charged state around the isoelectric point of the antibody, and to be electrostatically adsorbed to the porous body. The isoelectric point of the antibody is irregular in many cases, but it is preferable to adjust it appropriately. When the biological substance is made adsorbed on the surface of the particle or the whole porous body, usually, the kind, concentration, and pH of the buffer solution are optionally determined considering the characteristics of the biological substance. However, electrically charged substances will cause electrostatic repulsion against each other, and an immobilizable amount is limited when the substances are introduced into nano-size pores of the porous body.

Therefore, electrostatic repulsion among respective antibodies has been alleviated in the present invention by elevating the salt level of the buffer solution to increase the ionic strength of the antibody solution. By this method, the maximum immobilization amount has been greatly increased as compared with conventional methods. The pH of the buffer solution may be directly adjusted to the vicinity of the isoelectric point of the antibody as well in order to decrease electrostatic repulsion, and these adjustment methods are not limited. Alternatively, a method including calculating the amount to be absorbed and having antibodies adsorbed onto the vicinity of the pore entrance after having adsorbed the other organic substances such as a protein may be used. The method is not limited to the above methods.

In addition, even if an antibody or the like is immobilized, it cannot be used when an ingredient of the reaction solution is non-specifically adsorbed onto the other parts, and therefore, a method of suppressing this by any sort of method is necessary. In that case, there are a method of separately using a blocking agent and a method of modifying the carrier surface with another molecule. In the former case, BSA is the most common blocking agent. However, since it is necessary in the present invention to fill the mesopores which do not contribute to a reaction with a blocking agent, casein having a molecular diameter (4 nm) smaller than BSA, which has a large molecular diameter (15 nm), is preferably used.

As a blocking agent, organic substances other than antibodies, antigens or the fragments thereof are used, and examples thereof include casein. The size of the particle size of the organic substance is preferably smaller than the diameter of the mesopores.

EXAMPLES

Hereinbelow, the present invention is described in more detail but the present invention is not limited to the disclosure by these Examples.

Example 1

In this Example, mesoporous silica is prepared in which substantially uniform tube-like mesopores are formed in parallel to the minor axis direction of the rod in a porous material having macropores formed by branched rod-shaped silica three-dimensionally disposed in the shape of a net. And this is an example in which a Fab antibody which is an antibody fragment is adsorbed within a distance of a pore diameter from the pore entrance.

2.40 g of a triblock copolymer ($EO_{20}PO_{70}EO_{20}$; $HO(CH_2CH_2O)_{20}(CH_2CH(CH_3)O)_{70}(CH_2CH_2O)_{20}H$), a nonionic surfactant, was dissolved in 76.5 mL of distilled water. 7.5 mL of 36 mass % concentrated hydrochloric acid was added to this and stirred at room temperature for 30 minutes. After dissolution, the aqueous solution was cooled in an incubator kept from 18° C. to 30° C. and allowed to stand still for two hours. Then, 13.9 g of n-decane was added and stirred at room temperature for one day. 0.027 g of $NH_4F$ as a hydrolysis catalyst and 5.10 g of tetraethoxysilane (TEOS) were further added to this mixture and the mixture was used as a precursor solution. The final composition (molar ratio) of the precursor solution was TEOS:HCl:$EO_{20}PO_{70}EO_{20}$: $NH_4F$:n-decane:$H_2O$=0.25:0.9:0.004:0.007:1:42.9.

This precursor solution was stirred at the above temperature for one day, transferred into a pressure-resistant container and reacted at 100° C. for 48 hours. The obtained white precipitation was sufficiently washed with distilled water and vacuum dried. The obtained powder sample was fired at 500° C. in the air to decompose and remove the surfactant from within the pores. Removal of organic matters such as the surfactant was confirmed by an infrared absorption spectrum.

Figure 3:
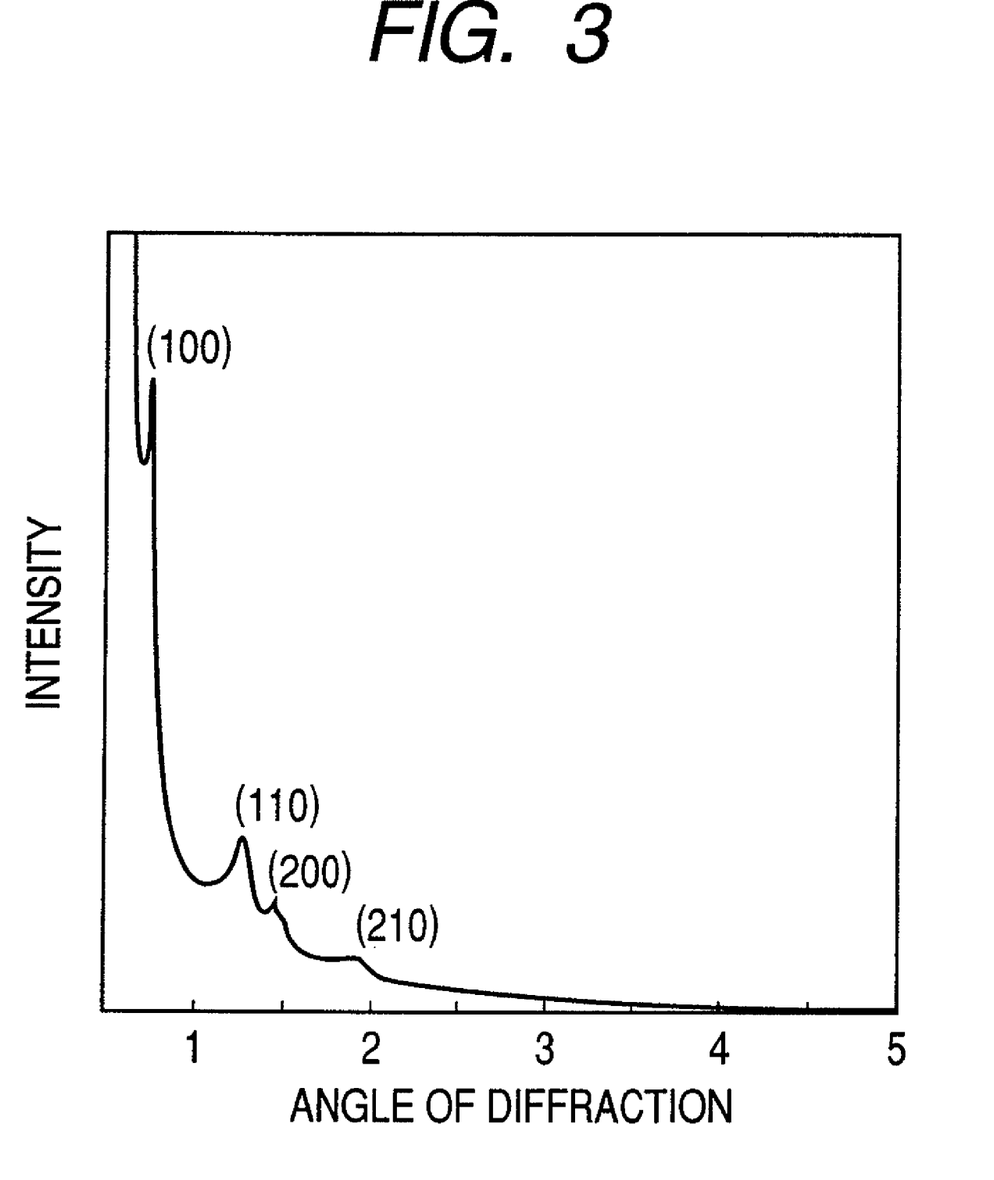
FIG. 3 illustrates the results of evaluation of mesoporous silica powder synthesized in Example 1 by an X ray diffraction method.

As a result of evaluating the synthesized mesoporous silica powder by X-ray diffraction method, a diffraction peak attributed to (100) face having a hexagonal structure with a face interval of 11.7 nm as well as diffraction peaks attributed to (110), (200) and (210) faces were recognized as shown in FIG. 3. These results show that the pore structure of this mesoporous silica has a hexagonal arrangement with a high regularity.

As a result of performing nitrogen adsorption-desorption isotherm measurement at 77 K, the profile of the adsorption isotherm was IV type in the IUPAC classification. The specific surface area determined by the B.E.T. method was 700 $m^2/g$, and the pore volume was 1.88 mL/g. Further, pore diameters were calculated by the BJH method from the result of this adsorption isotherm and the pore size distribution of mesoporous silica synthesized in this example has a narrow distribution having a single peak at 14.1 nm, and about 90% of the pores fell in a range having a width of 10 nm in this distribution.

Figure 4:
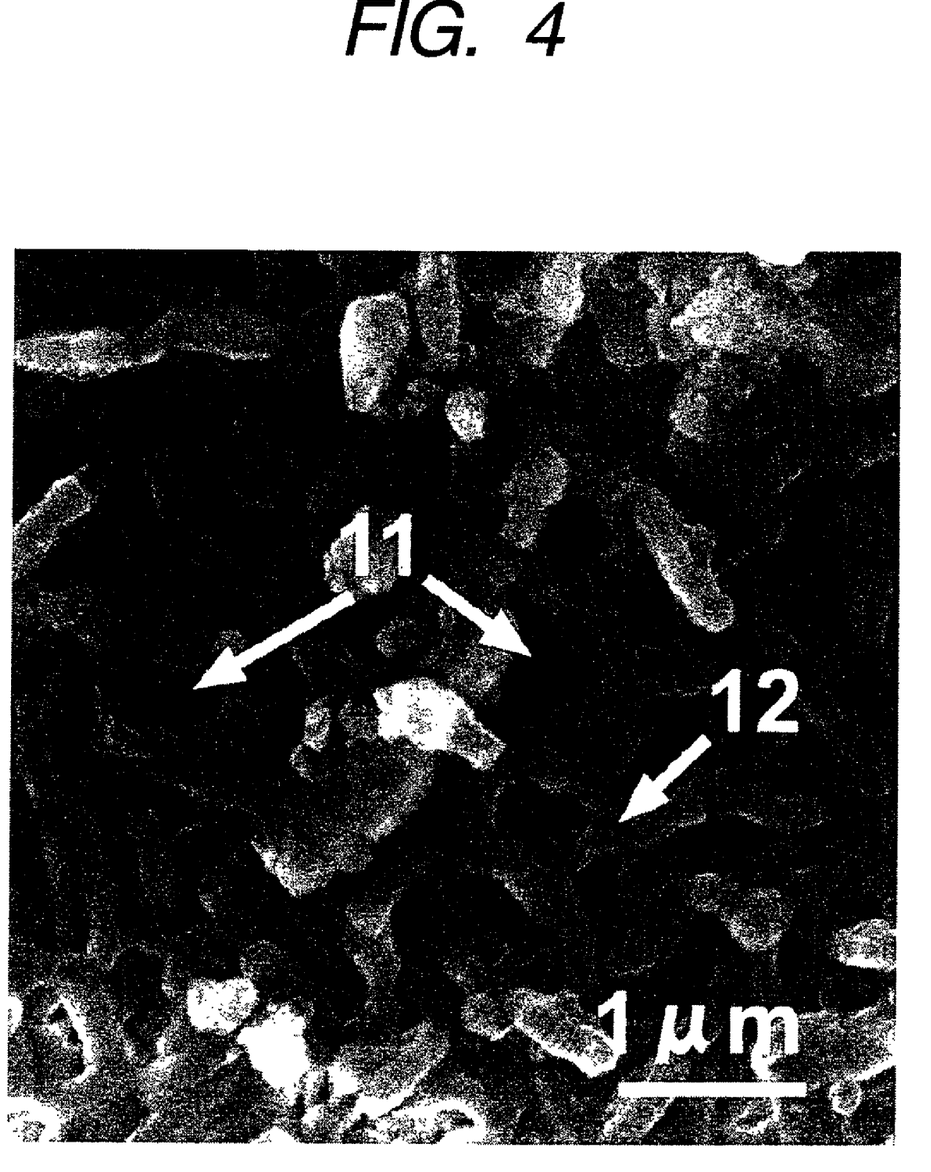
FIG. 4 is a scanning electron micrograph of a mesoporous silica material synthesized in Example 1.
Figure 5:
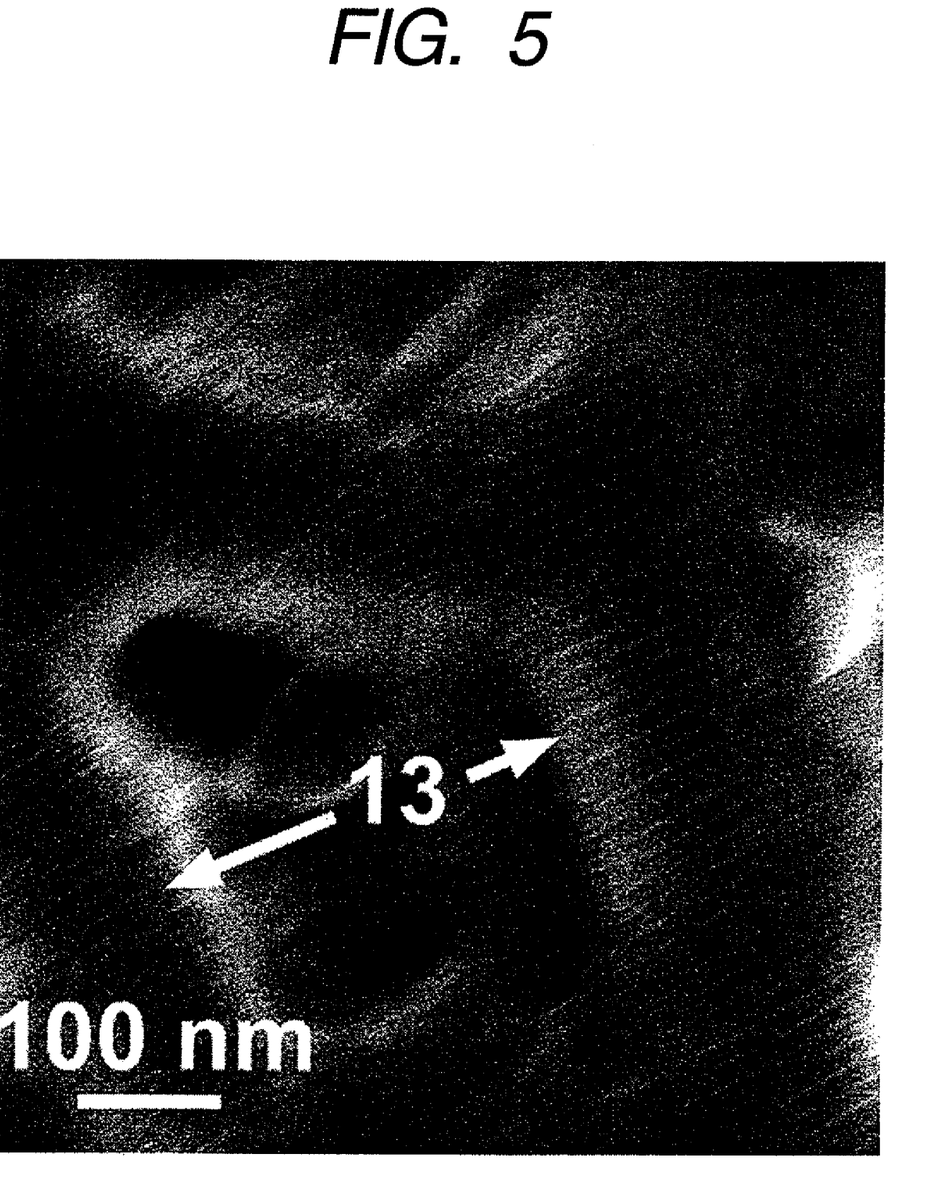
FIG. 5 is a scanning electron micrograph of a mesoporous silica material synthesized in Example 1.
Figure 6:
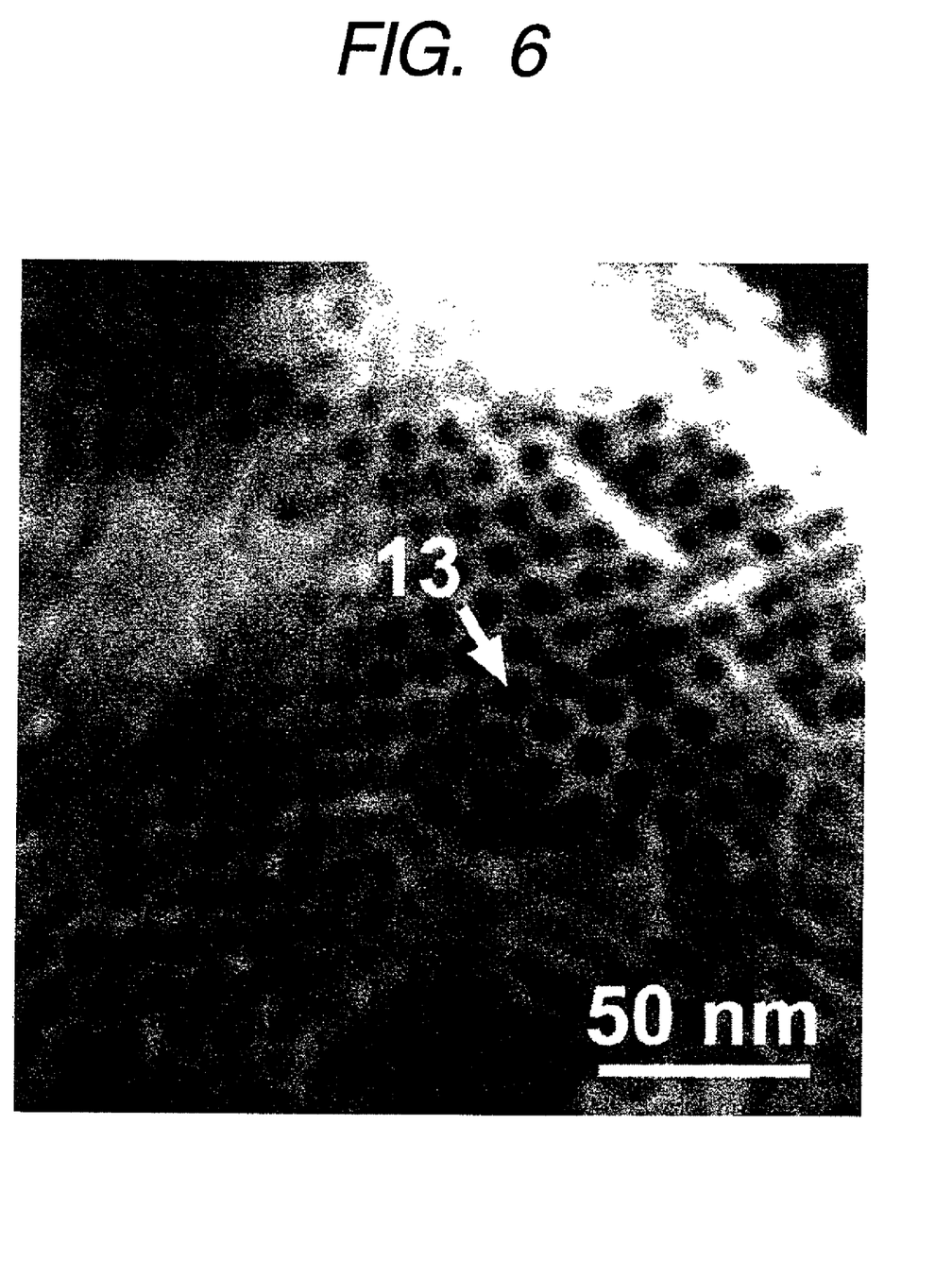
FIG. 6 is a scanning electron micrograph of a mesoporous silica material synthesized in Example 1.

The powder was then subjected to observation with a scanning electron microscope (SEM) and a dendritic structure with a number of branched rods and a structure in which these dendritic structures are disposed in three dimension to form a network were observed as shown in FIG. 4. Macropores of 300-500 nm in the size are formed in the spaces among the branched rods of these dendritic structures. The diameter of the rods was from 200 nm to 300 mm. Higher power SEM observation revealed that tube-like mesopores having a diameter of 14 nm oriented in the direction along the minor axis of the rods of the dendritic structure body as shown in FIG. 5, and it was confirmed that the ratio of the pore size and the length of the tube-like pore was not less than 5 times and not more than 30 times. Further, relatively uniform tube-like mesopores formed a honeycomb packed pore structure in the cross section as shown in FIG. 6.

Then, the mesoporous silica prepared as above was used and lysozyme was adsorbed within the mesopores to artificially fill the inside of the pores with a protein other than Fab and then antigen-antibody reaction was performed.

Lysozyme was prepared at 1.0 mg/mL, 0.4 mg/mL, 0.2 mg/mL with a 10 mM phosphate buffer of pH 7.4, and, and 2.0 mg of mesoporous silica synthesized above was added to 1 mL of this solution. This mixture solution was stirred with a shaker at 4° C. for 24 hours and lysozyme was adsorbed within the pores of the mesoporous silica. After the stirring was finished, centrifugation at 4° C. for 10 minutes at 20000 g was performed and lysozyme-immobilized silica was obtained. Utilizing absorption maximum at 280 nm in the supernatant solution before and after the adsorption, absorbed amount of lysozyme to the mesoporous silica was calculated. As a result, samples with immobilized amount of (A) 450 mg/g, (B) 170 mg/g and (C) 80 mg/g were respectively obtained.

Then, Fab antibody of antigoat IgG labelled with HRP was adsorbed on this lysozyme-immobilized mesoporous silica.

The Fab antibody was prepared at 0.5 mg/mL with a 10 mM phosphate buffer of pH 7.4; and lysozyme-immobilized mesoporous silica prepared above was added thereto. This mixture was stirred with a shaker at 4° C. for 24 hours and Fab was adsorbed within the pores of the mesoporous silica. After the stirring was finished, centrifugation at 4° C. for 10 minutes at 20000 g was performed and Fab-antibody-immobilized silica was obtained. Utilizing absorption maximum at 405 nm in the supernatant solution before and after the adsorption, absorbed amount of Fab antibody to the mesoporous silica was calculated. The absorbed amount of Fab was calculated as (A) 60 mg/g, (B) 100 mg/g and (C) 170 mg/g respectively. The absorbed amount of Fab increased in inverse proportion to the absorbed amount of lysozyme. When the respective samples were observed with an immunity electron microscope, the absorbed amount in the vicinity of the pore entrance was almost the same amount in all the samples. These results demonstrate that lysozyme selectively adsorbs from the depths of the pores.

Then, casein was adsorbed to prevent non-specific absorption of antigens or the like to the samples to which Fab antibodies were adsorbed. The thus prepared mesoporous silica to which polyclonal Fab antibodies of lysozyme/anti-goat IgG were immobilized was added to a goat IgG solution prepared at 1 mg/mL with a 10 mM phosphate buffer (pH 7.4). Then the mixture was stirred at 4° C. for two hours and centrifuged at 4° C. for 5 minutes at 20000 g. The binding activity of Fab antibody to goat IgG was calculated by measuring absorbance of this supernatant liquid.

As a result, binding activity from 100 mg/g to 110 mg/g was shown for the samples (A) to (C). Mouse IgG which was non-specific to the above Fab was used as a negative control. The absorbed amount in this Example was clearly higher than the control, demonstrating that IgG antibody was effectively immobilized and the antigen-antibody reaction effectively occurred after immobilization. Binding activity is approximately constant in three samples, although the absorbed amount of the Fab antibody was different for these samples, and it is therefore considered that only Fab which exists in the vicinity of the surface contributes to an antigen-antibody reaction. The results of TEM observation of a similar antigen-antibody reaction using HRP-labelled goat IgG support these results. Therefore, since only Fab in the vicinity of the pore surface participates in an antigen-antibody reaction, utilization efficiencies of immobilized Fab (bound IgG/immobilized Fab) are calculated as (A) 40%, (B) 27% and (C) 17%. It has been revealed that Fab can be utilized effectively by filling the pore deeper than the pore diameter with proteins other than Fab.

Example 2

This Example is an example performing antigen-antibody reaction using mesoporous silica in which Fab antibodies of antigoat IgG were immobilized prepared in Example 1.

The mesoporous silica in which Fab antibodies of antigoat IgG were immobilized prepared in Example 1 was added to a goat IgG solution prepared at 1 mg/mL with a 10 mM phosphate buffer (pH 7.4). Then the mixture was stirred at 4° C. for two hours and centrifuged at 4° C. for 5 minutes at 20000 g. The binding activity of Fab antibody to goat IgG was calculated by measuring absorbance of this supernatant liquid.

Figure 7:
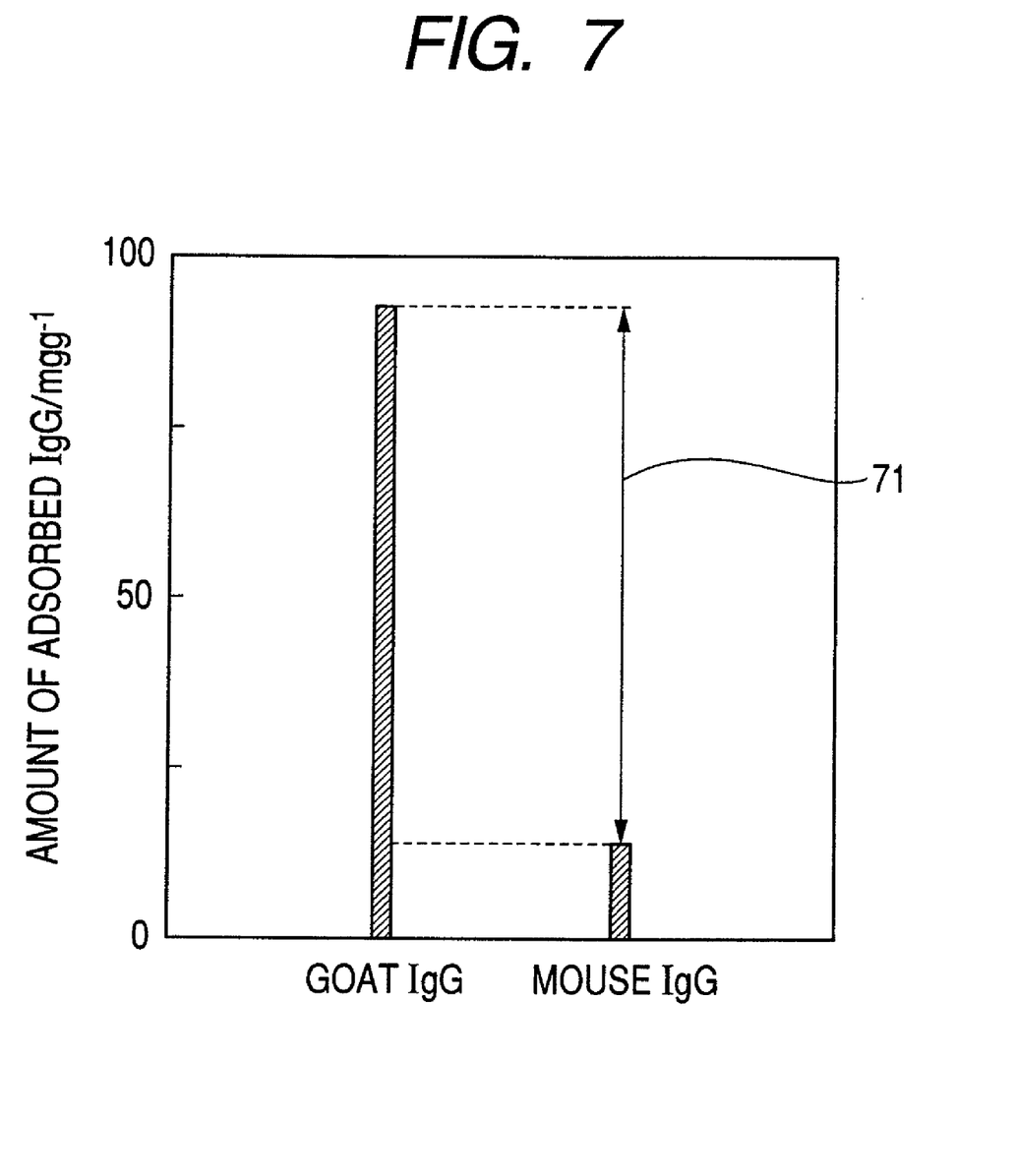
FIG. 7 illustrates the results of antigen-antibody reaction in Example 2.

Mouse IgG which was non-specific to the above Fab was used as a negative control, and the binding activity 71 was compared based on the difference between them. The results are shown in FIG. 7. The absorbed amount in this Example was clearly higher than the control, demonstrating that the antibodies were effectively immobilized and the antigen-antibody reaction effectively occurred after they were immobilized. When mesoporous silica in which only 120 mg/g of Fab antibody were adsorbed, which was used in Example 1, was used, specific adsorption of IgG was hardly recognized as in the control. It is considered that, in this case, an antigen-antibody reaction did not occur since there were no Fab antibody at the pore entrance. The results of TEM observation of a similar antigen-antibody reaction using HRP-labelled goat IgG support these results.

In addition, considering the size of IgG (15 nm) and the pore size (14 nm), it can be presumed that Fab and IgG cause the one-to-one antigen-antibody reaction of this Example at the pore entrance. Accordingly, the number of adsorbed Fab antibody molecules/the number of the entrance of mesopores was calculated, and it was found that Fab immobilized at the pore entrance could be used with a probability from about 60% to 80%. The Fab antibody once immobilized has flexibility in immobilization, and it is presumed that they were re-oriented and caused antigen-antibody reaction.

Comparative Example 1

As a comparative example, mesoporous silica in which tube-like mesopores having length 30 times or more of the pore size were formed was synthesized and the amount of immobilization of Fab antibodies was measured. Such mesoporous silica is described in Journal of the American Chemical Society, Vol. 126, page 7740 and can be obtained by changing the ratio of decane/P123 (wt/wt).

2.40 g of a triblock copolymer triblock copolymer ($EO_{20}PO_{70}EO_{20}$; $HO(CH_2CH_2O)_{20}(CH_2CH(CH_3)O)_{70}(CH_2CH_2O)_{20}H$), a nonionic surfactant was dissolved in 76.5 mL of distilled water. 7.5 mL of 36 wt % concentrated hydrochloric acid was added to this and stirred at room temperature for 30 minutes. Then, 0.96 g of n-decane was added and stirred at room temperature for two hours. 0.027 g of $NH_4F$ as a hydrolysis catalyst and 5.10 g of tetraethoxysilane (TEOS) were further added to this mixture and the mixture was used as a precursor solution. The final composition (molar ratio) of the precursor solution was $TEOS:HCl:EO_{20}PO_{70}EO_{20}:NH_4F:n\text{-decane}:H_2O=0.25:0.9:0.004:0.007:1:42.9$.

This precursor solution was stirred at 40° C. for 20 hours, and reacted at 100° C. for 48 hours. The obtained white precipitation was sufficiently washed with distilled water and vacuum dried.

The obtained powder sample was fired at 500° C. in the air to decompose and remove the surfactant from within the pores. As a result of evaluating the synthesized mesoporous silica powder by X-ray diffraction method, a diffraction peak attributed to (100) face having a hexagonal structure as well as diffraction peaks attributed to (110), (200) and (210) faces were recognized.

As a result of performing nitrogen adsorption-desorption isotherm measurement at 77 K, the profile of the adsorption isotherm was IV type in the IUPAC classification. The specific surface area determined by the B.E.T. method was 650 $m^2/g$, and the pore volume was 1.59 mL/g. Further, pore diameters were calculated by BJH method from the result of this adsorption isotherm and the pore size distribution of mesoporous silica synthesized in this Example has a narrow distribution having a single peak at 10.4 nm, and about 90% of the pores fell in a distribution range of 10 nm.

The powder was then subjected to observation with SEM, and although network-shaped structure was not formed, innumerable rod-shaped fine particles were recognized. The rod-shaped structural body had a diameter from 150 nm to 300 nm and a length of around 500 nm. Higher power SEM observation revealed that tube-like mesopores having a diameter of 10 nm oriented in the direction along the major axis of the rod-shaped structure, and it was confirmed that the ratio of the pore size and the length of the pore was not less than 30 times.

Next, Fab antibodies were immobilized within the mesopores of this mesoporous silica as in Example 1.

The Fab antibodies were prepared at 0.01 mg/mL to 1.0 mg/mL with a 10 mM phosphate buffer of pH 7.4, and, and 2.0 mg of mesoporous silica synthesized above was added to 1 mL of this solution. This mixture solution was stirred with a shaker at 4° C. for 24 hours and Fab was adsorbed within the pores of the mesoporous silica. After the stirring was finished, centrifugation at 4° C. for 10 minutes at 20000 g was performed and Fab-antibody-immobilized silica was obtained. Utilizing absorption maximum at 280 nm in the supernatant solution before and after the adsorption, absorbed amount of Fab antibody to the mesoporous silica was calculated. The Fab antibody showed a little immobilized amount of around 50 mg/g. The nitrogen adsorption behavior to the pores before and after the Fab adsorption observed with a nitrogen adsorption measuring apparatus slightly changed suggesting that Fab antibodies were immobilized within the pores.

In addition, casein was adsorbed to prevent non-specific absorption of antigens or the like to the samples to which Fab antibodies were adsorbed. The mesoporous silica to which Fab antibodies were adsorbed by the above method was washed with distilled water and dispersed in 1% casein solution prepared with a phosphate buffer (pH 7.4) and stirred at 4° C. for five hours. After the stirring was finished, the mixture was centrifuged at 4° C. for 5 minutes at 20000 g and Fab-antibody-immobilized silica was obtained.

Then, in order to measure antigen-antibody reaction, this mesoporous silica to which Fab antibodies of antigoat IgG were immobilized was added to a goat IgG solution prepared at 1 mg/mL with a 10 mM phosphate buffer (pH 7.4). Then the mixture was stirred at 4° C. for two hours and centrifuged at 4° C. for 5 minutes at 20000 g. The binding activity of Fab antibody to goat IgG was calculated by measuring absorbance of this supernatant liquid.

Mouse IgG which was non-specific to the above Fab was used as a negative control, and the binding activity was compared based on the difference between them. However, no significant difference from the control was recognized. It is considered that no antigen-antibody reaction occurred since the Fab antibodies were not present at the pore entrance.

The present invention is not limited to the above embodiments and various changes and modifications can be made within the spirit and scope of the present invention. Therefore, to apprise the public of the scope of the present invention, the following claims are made.

This application claims priority from Japanese Patent Application No. 2006-327461 filed on Dec. 4, 2006, which is hereby incorporated by reference herein.

The invention claimed is:

1. A protein-immobilized carrier comprising a porous body, comprising:
    rods having mesopores;
    an organic substance which is adsorbed inside the mesopores and which is smaller than a size of the mesopores; and
    a protein immobilized by physical adsorption on a region of each mesopore from an entrance of the mesopore to the same depth as the size of the mesopores,
    wherein the protein is selected from a group consisting of an antibody, an antigen and a fragment of the antibody or the antigen,
    wherein the organic substance is a substance other than the protein, and
    wherein the rods form a dendritic structure and are three dimensionally disposed in a shape of a net.

2. The protein-immobilized carrier according to claim 1, wherein a part of the mesopores adsorbs only the organic substance and does not immobilize the protein.

3. The protein-immobilized carrier according to claim 1, wherein the size of the mesopores is in the range of 7 nm to 30 nm.

4. The protein-immobilized carrier according to claim 1, wherein the mesopores have a length of 5 times and 30 times of the size of the mesopores.

5. The protein-immobilized carrier according to claim 1, wherein the mesopores are disposed in a honeycomb shape.

6. The protein-immobilized carrier according to claim 1, wherein the mesopores have a pore size distribution determined by nitrogen gas adsorption measurement having a single maximum and not less than 60% of all the mesopores fall within the pore size distribution range of not more than 10 nm.

7. The protein-immobilized carrier according to claim 1, wherein at least one diffraction peak in X ray diffraction analysis exists in an angle region corresponding to a structural period of not less than 1 nm.

8. The protein-immobilized carrier according to claim 1, wherein a material constituting a pore wall of the porous body comprises silicon as an ingredient.

9. The protein-immobilized carrier according to claim 8, wherein the material constituting a pore wall is silica.

10. The protein-immobilized carrier according to claim 1, wherein the organic substance is a protein which is different from the immobilized protein.

11. The protein-immobilized carrier according to claim 1, wherein the rods comprise silica.

12. The protein-immobilized carrier according to claim 1, wherein the mesopores are tube-shaped, are disposed in parallel with the minor axis direction of the rods, and are stacked in layers in the major axis direction of the rods.

* * * * *